US009070270B2

(12) United States Patent
Kreiner et al.

(10) Patent No.: US 9,070,270 B2
(45) Date of Patent: *Jun. 30, 2015

(54) METHODS, SYSTEMS, AND PRODUCTS FOR TRACKING SURGICAL ITEMS (71) Applicant: AT&T Intellectual Property I, L.P., Atlanta, GA (US)

(72) Inventors: Barrett M. Kreiner, Woodstock, GA (US); Jonathan L. Reeves, Rosewell, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/331,129

(22) Filed: Jul. 14, 2014

(65) Prior Publication Data

US 2014/0324643 A1    Oct. 30, 2014

Related U.S. Application Data (63) Continuation of application No. 13/205,380, filed on Aug. 8, 2011, now Pat. No. 8,781,920, which is a continuation of application No. 12/823,183, filed on Jun. 25, 2010, now Pat. No. 7,996,286, which is a continuation of application No. 12/566,709, filed on Sep. 25, 2009, now Pat. No. 7,774,244, which is a continuation of application No. 11/641,135, filed on Dec. 19, 2006, now Pat. No. 7,617,137.

(51) Int. Cl.
*G06F 19/00* (2011.01)
*G06F 7/00* (2006.01)
*G08B 13/14* (2006.01)
*G08B 21/02* (2006.01)
*A61B 19/00* (2006.01)
*G06Q 10/08* (2012.01)
*G06Q 30/04* (2012.01)
*G06Q 50/22* (2012.01)

(52) U.S. Cl.
CPC ............... *G08B 21/02* (2013.01); *A61B 19/44* (2013.01); *A61B 2019/448* (2013.01); *G06Q 10/087* (2013.01); *G06Q 30/04* (2013.01); *G06Q 50/22* (2013.01)

(58) Field of Classification Search
CPC ..... A61B 19/5244; A61B 19/44; A61B 19/56
See application file for complete search history.

(56) References Cited

U.S. PATENT DOCUMENTS 4,114,601 A * 9/1978 Abels ............................. 600/20
5,190,059 A * 3/1993 Fabian et al. ................. 128/899

(Continued)

OTHER PUBLICATIONS

Zacks et al, 7 Startups Graduate with Honors, Sep. 2001, Tehcnology Review, vol. 104 No. 7, pp. 71-78.*

(Continued)

*Primary Examiner* — Matthew Gart
*Assistant Examiner* — Talia Crawley (57) ABSTRACT

Methods, systems, and products track equipment used during surgical procedures. An allowable zone associated with a surgical procedure is identified. The allowable zone determines where surgical items may be used during the procedure. A location of a surgical item is determined. When the location is outside the allowable zone, an alarm is triggered to indicate the surgical item is moving outside the allowable zone towards an area in which the surgical item may not be used.

20 Claims, 8 Drawing Sheets

(56) References Cited

U.S. PATENT DOCUMENTS

| | | | |
|---|---|---|---|
| 5,931,824 A * | 8/1999 | Stewart et al. | 604/358 |
| 6,076,007 A * | 6/2000 | England et al. | 600/424 |
| 6,366,206 B1 * | 4/2002 | Ishikawa et al. | 340/573.1 |
| 6,400,272 B1 * | 6/2002 | Holtzman et al. | 340/572.1 |
| 6,424,262 B2 * | 7/2002 | Garber et al. | 340/572.3 |
| 6,600,418 B2 * | 7/2003 | Francis et al. | 340/572.1 |
| 6,640,214 B1 * | 10/2003 | Nambudiri et al. | 705/26 |
| 6,669,089 B2 * | 12/2003 | Cybulski et al. | 235/385 |
| 6,768,419 B2 * | 7/2004 | Garber et al. | 340/572.4 |
| 6,809,645 B1 * | 10/2004 | Mason | 340/572.1 |
| 6,861,954 B2 * | 3/2005 | Levin | 340/572.1 |
| 6,900,731 B2 * | 5/2005 | Kreiner et al. | 340/572.1 |
| 7,001,366 B2 | 2/2006 | Ballard | |
| 7,019,650 B2 * | 3/2006 | Volpi et al. | 340/572.1 |
| 7,142,118 B2 * | 11/2006 | Hamilton et al. | 340/572.1 |
| 7,307,530 B2 * | 12/2007 | Fabian et al. | 340/572.1 |
| 7,557,710 B2 * | 7/2009 | Sanchez et al. | 340/572.1 |
| 7,617,137 B2 | 11/2009 | Kreiner et al. | |
| 7,774,244 B2 | 8/2010 | Kreiner et al. | |
| 7,996,286 B2 | 8/2011 | Kreiner et al. | |
| 2002/0067263 A1 * | 6/2002 | Tafoya et al. | 340/572.1 |
| 2002/0143320 A1 * | 10/2002 | Levin | 606/1 |
| 2003/0066537 A1 * | 4/2003 | Fabian et al. | 128/899 |
| 2003/0105394 A1 * | 6/2003 | Fabian et al. | 600/407 |
| 2004/0084525 A1 * | 5/2004 | Kreiner et al. | 235/384 |
| 2004/0129279 A1 * | 7/2004 | Fabian et al. | 128/899 |
| 2004/0201479 A1 * | 10/2004 | Garber et al. | 340/572.1 |
| 2004/0250819 A1 * | 12/2004 | Blair et al. | 128/899 |
| 2007/0093709 A1 * | 4/2007 | Abernathie | 600/407 |
| 2007/0290030 A1 * | 12/2007 | Fox et al. | 235/375 |
| 2008/0237341 A1 | 10/2008 | Fleck et al. | |

OTHER PUBLICATIONS

Nursing Management, Medical Patents: Remote Monitoring: Expanding a successful system, Capuano et al: May 1997. vol. 28, Issue 5; pp. 40A, 2pgs.*

Nursing Management, Medical Patents: Remote Monitoring: Expanding a successful system, Capuano et al: May 1997, vol. 28, Issue 5; pp. 40A, 2pgs.

Capuano et al., "Nursing Management, Medical Patents: Remote Monitoring: Expanding a successful system", May 1997, vol. 28, Issue 5, pp. 40A, 2pgs.

* cited by examiner

METHODS, SYSTEMS, AND PRODUCTS FOR TRACKING SURGICAL ITEMS

CROSS-REFERENCE TO RELATED APPLICATIONS

This application is a continuation of U.S. application Ser. No. 13/205,380, filed Aug. 8, 2011, now issued as U.S. Pat. No. 8,781,920, which is a continuation of U.S. application Ser. No. 12/823,183, filed Jun. 25, 2010, now issued as U.S. Pat. No. 7,996,286, which is a continuation of U.S. application Ser. No. 12/566,709, filed Sep. 25, 2009, now issued as U.S. Pat. No. 7,774,244, which is a continuation of U.S. application Ser. No. 11/641,135, filed Dec. 19, 2006, and now issued as U.S. Pat. No. 7,617,137, with all the above cited applications incorporated herein by reference in their entirety.

BACKGROUND

The present invention relates generally to the use of radio frequency identification (RFID) devices, and more particularly, to systems and methods used by these devices to support improvements in a surgical system.

In a surgical suite it is important to keep track of all equipment used during an operation. Depending on the equipment being used, a typical tracking method involves tracking items via manual counting by operating personnel present in the suite. For example, this manual process could involve counting surgical sponges in and then counting surgical sponges out upon completion of the operation. However, there are downsides to this manual method. Mistakes can be made which can have both a hazardous outcome for the patient and pose a significant financial loss for the responsible institution. Additionally this recount method is time consuming and tedious. Accordingly, other methods have been developed to address this problem.

One such method used involves the use of a radiopaque. A radiopaque is a material that can be detected through the use of x-rays. Continuing with the sponge example from above, a radiopaque thread is attached to a sponge. Upon completion of the operation an x-ray device is used to scan the patient. If the x-ray device detects a radiopaque thread, this might mean that a sponge was left inside of the patient. While it is good that the sponge was found before the patient left the hospital, there are still some significant cons to this method. For example, to retrieve the sponge, the patient may need to be re-operated upon. Another potential problem with using a radiopaque thread is that the thread could be disposed behind a bone, which could hide the radiopaque thread from the x-ray device.

In addition to tracking surgical items to ensure the safety of the patient, another important aspect of the surgical suite is management of the various medical processes associated with the people and equipment as a whole. Keeping track of equipment, people, surgical tools and disposable materials is a complex job. Therefore an efficient system for managing the whole would be a useful improvement.

A basic Radio Frequency Identification (RFID) system typically includes an antenna (or equivalent), a transceiver and a transponder. RFID tags are often attached to items for tracking purposes. These RFID devices can come in a wide variety of sizes, and can contain a significant amount of data as desired. RFID tags, when coupled to equipment found in a surgical suite, provide a mechanism for resolving the problems described above and for improving practices in a surgical suite. RFID tags have been disclosed for use in the surgical setting. For example U.S. Pat. No. 7,019,650 B2, the disclosure of which is incorporated here by reference, describes an interrogator, a method of discerning metal and radio frequency identification (RFID) objects, and an interrogation system employing the same.

Exemplary embodiments described herein address the need for more efficient systems and methods using RFID devices for both tracking surgical equipment used during surgery and improving the whole surgical suite process using information available from RFID tags and other devices.

SUMMARY

According to one exemplary embodiment, a system for tracking surgical items includes a plurality of surgical items, wherein each item has an associated RFID tag, a surgical table, wherein the surgical table has a sensor capable of reading the RFID tags associated therewith, a computing device in communication with the sensor, and a database in communication with the computing device, wherein the computing device performs at least one of the following functions based on information received from the sensor and the database: (a) confirming a type of surgical procedure to be performed, (b) determining whether one or more of the plurality of surgical items are located outside of at least one allowable zone, the at least one allowable zone being determined based on a type of surgical procedure to be performed, (c) determining whether the plurality of surgical items include a predetermined set of surgical items associated with the type of surgical procedure to be performed, (d) tracking disposable ones of the plurality of surgical items based upon their usage during the surgical procedure, and (e) compiling billing information associated with usage of the plurality of surgical items during the surgical procedure.

According to another exemplary embodiment, a method for tracking a plurality of surgical items includes the steps of providing a plurality of surgical items, wherein each item has an associated RFID tag, interrogating the RFID tags to determine a location and identity of the plurality of surgical items, and performing at least one of the following functions based on information received from the interrogating step: (a) confirming a type of surgical procedure to be performed, (b) determining whether one or more of the plurality of surgical items are located outside of at least one allowable zone, the at least one allowable zone being determined based on the type of surgical procedure to be performed, (c) determining whether the plurality of surgical items include a predetermined set of surgical items associated with the type of surgical procedure to be performed, (d) tracking disposable ones of the plurality of surgical items based upon their usage during the surgical procedure, and (e) compiling billing information associated with usage of the plurality of surgical items during the surgical procedure.

According to yet another exemplary embodiment, a system for tracking a plurality of surgical items includes means for interrogating RFID tags to determine a location and identity of a plurality of surgical items, and means for performing at least one of the following functions based on information received from the interrogating means: (a) means for confirming a type of surgical procedure to be performed; (b) means for determining whether one or more of the plurality of surgical items are located outside of at least one allowable zone, the at least one allowable zone being determined based on the type of surgical procedure to be performed, (c) means for determining whether the plurality of surgical items include a predetermined set of surgical items associated with the type of surgical procedure to be performed, (d) means for tracking disposable ones of said plurality of surgical items based upon their usage during the surgical procedure, and (e) means for compiling billing information associated with usage of the plurality of surgical items during the surgical procedure.

BRIEF DESCRIPTION OF THE DRAWINGS

The accompanying drawings illustrate exemplary embodiments of the present invention, wherein.

DETAILED DESCRIPTION

The following detailed description of the invention refers to the accompanying drawings. The same reference numbers in different drawings identify the same or similar elements. Also, the following detailed description does not limit the invention. Instead, the scope of the invention is defined by the appended claims.

Radio frequency identification (RFID) systems typically include a transceiver and one or more transponders (RFID tags). The transceiver emits radio signals to activate the RFID tags and to read/write data to them via an antenna. The transceiver typically has an associated decoder for decoding data received from an RFID tag. The combination of an antenna, transceiver and decoder is sometimes referred to as an "interrogator" in an RFID system. The transponder can be electronically programmed with any desirable information, the constraint being size. In a typical RFID system, the interrogator transmits radio waves (range dependent upon power and frequency). When an RFID tag enters the zone in which the interrogator is transmitting, it detects the decoder's activation signal. This causes the RFID tag to transmit its data signal back to the interrogator. RFID tags can be active (i.e., have their own power source for generating the data signal) or passive (i.e., use electromagnetic energy induced in the RFID tag by receipt of the activation signal to generate the data signal). The decoder then decodes the data on the RFID tag. This decoded data is then typically transmitted to a computing system that is in communication with the decoder.

Figure 1:
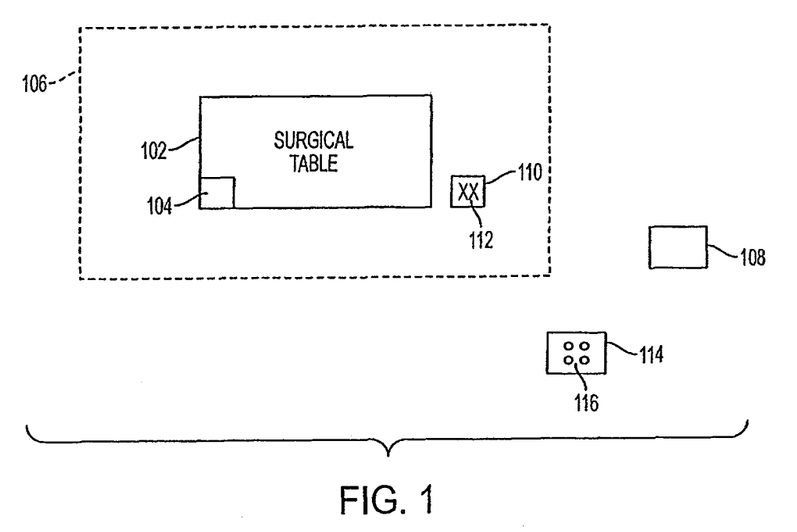
FIG. 1 depicts a surgical suite according to exemplary embodiments.

According to one exemplary embodiment of the present invention, a surgical table has the ability to query RFID devices that come within its active zone. To provide a comprehensive system which facilitates some of the work flow features described below, it may be useful for all (or substantially all) tools, equipment or materials (collectively referred to herein as "surgical items") used in the surgical process to have an RFID tag either embedded within the tool, equipment or materials or attached to the tool, equipment or materials. This method of utilizing RFID tags improves the ability to track items in the surgical suite, particularly those items that come close to the patient. An example of a surgical suite according to an exemplary embodiment is described with respect to FIG. 1. Therein, surgical table 102 has an attached or embedded sensor 104, e.g., an interrogator as described above, for interacting with RFID tags. Any item with an RFID tag that crosses boundary 106 towards surgical table 102 is noticed by sensor 104. For example, upon tray 110 are surgical tools 112. These surgical tools 112 each have an associated RFID device and, therefore, sensor 104 "knows" where these devices are because these surgical tools 112 are within boundary 106 such that sensor 104 can transmit to, and receive from, the RFID tags associated with each of the surgical tools 112. Upon tray 114 rest surgical tools 116. These surgical tools are not "known" by sensor 104 because surgical tools 116 are outside of boundary 106. However, to the extent that the range of the sensor(s) 104 associated with surgical table 102 is insufficient to encompass the entire area within which the devices, equipment and materials to be used in a particular procedure, additional sensor(s) may be distributed about the suite. Surgical table 102 is also in communication with a computing device 108. Computing device 108 and surgical table 102 share information relating to the surgery and RFID tagged items.

Figure 2A:
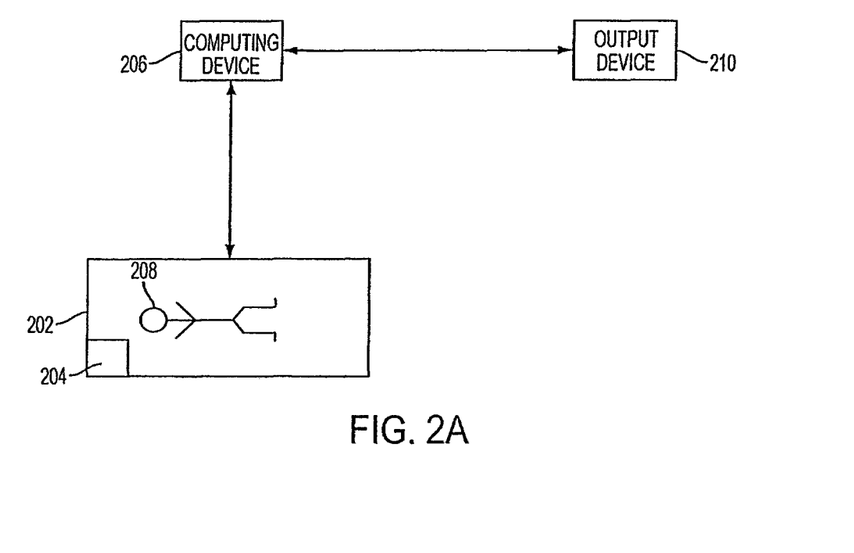
FIG. 2(a) depicts a computing system in communication with a surgical table and an output device according to exemplary embodiments.

According to another exemplary embodiment of the present invention, a surgical table is in communication with a computing device. This surgical table is equipped with a sensor(s) for reading RFID tags that are attached to surgical equipment. The computing device is programmed with information regarding the upcoming surgery such as type of surgery, location of surgery on the patient, potential tools/equipment to be used during the expected surgery and alarm zones. Exemplary uses of this system will be described with respect to FIGS. 2(a) and 2(b). Initially there is a surgical table 202, with an attached/embedded sensor 204 for interacting with RFID tags, in communication with computing device 206. Computing device 206 contains information regarding the upcoming surgery including, for example, patient identification information, identification of the procedure(s) to be performed and identification of the device(s), equipment(s) or material(s) to be used during the procedure. Patient 208 can have an attached RFID tag (not shown) that also describes relevant information, such as the patient's identification and type of surgery to be performed. This RFID tag (not shown) is queried by sensor 204. The information gathered by sensor 204 is then communicated to computing device 206. Computing device 206 then compares the received data to the information it previously received relating to the upcoming surgery. If the information does not match, an alarm could be produced on or by output device 210 warning people in the surgical suite not to proceed with the operation.

Figure 2B:
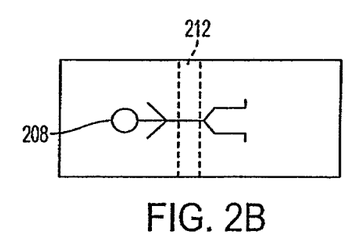
FIG. 2(b) illustrates an allowable zone according to exemplary embodiments.

Assuming that the information matches, certain parameters related to the upcoming operation are created by computing device 206. For example, assuming that the upcoming operation is an appendix removal, the computing device could identify one or more allowable zones in which certain surgical tools may be used during the appendix removal procedure (or, conversely, zones in which surgical tools may not be used). Referring now to FIG. 2(b), an exemplary allowable zone 212 is depicted with respect to patient 208. If a doctor were to move a surgical tool outside of zone 212, towards a foot for example, an alarm would be triggered. This alarm could be audible, visual or both and displayed on or by output device 210 or on the surgical tool itself which has left the allowable zone. Similar to matching a patient 208 with data in computing system 206, surgical tools (not shown) could be matched to data in computing system 206 and the presence of surgical tools which are inappropriate for use in the surgical procedure which is next to be performed in this particular surgical room or suite can be identified and brought to the attention of medical personnel, e.g., by way of a display 210 attached to computing device 206.

Figure 3:
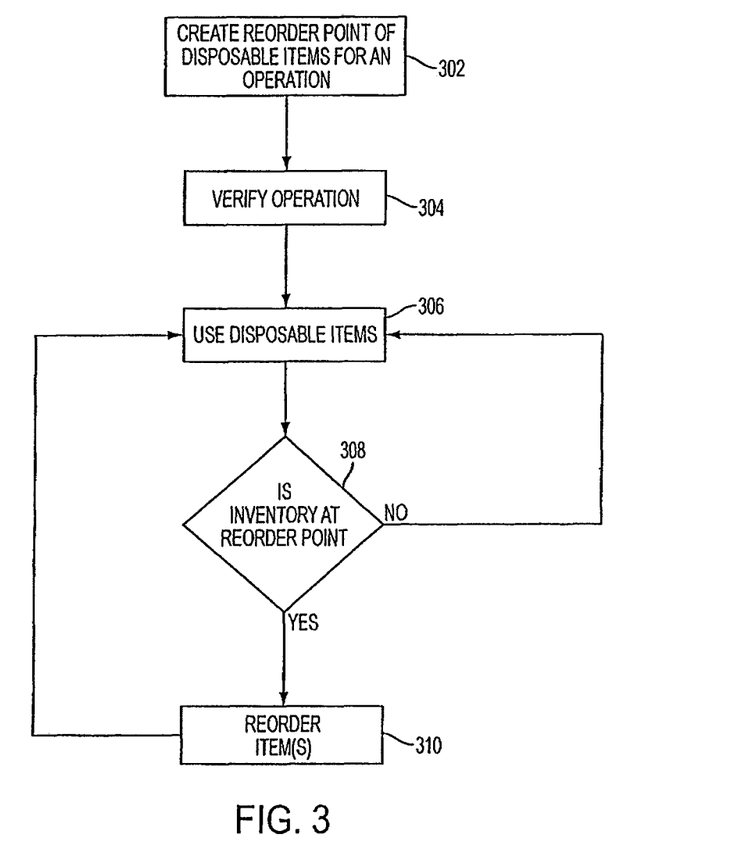
FIG. 3 is a flow chart illustrating an inventory management system according to exemplary embodiments.

According to another exemplary embodiment of the present invention there is a computing system that manages inventories of equipment before, during and after an operation. This computing system is in communication with both the surgical table and at least one output device. This system can work in tandem with the surgical suite described above, where each piece of disposable equipment has an attached RFID tag and the surgical table has a sensor to track RFID tagged equipment that enters its interrogation zone. This exemplary process will be described using the flow chart of FIG. 3. Initially a reorder point for a type of disposable item used in an operation is created at step 302. Prior to beginning the operation, the type of operation is verified and cross checked to ensure that it matches with the next procedure previously programmed into the computer system at step 304. The surgical operation then begins, and as needed, disposable items such as sponges, are used at step 306. Each time a disposable item is used, the computing system determines if the remaining inventory of the disposable item is at the reorder point step 308. If the remaining inventory is above the reorder point nothing occurs (except ongoing inventory tracking). If the remaining inventory is at or below the reorder point, new inventory is automatically ordered at step 310 in the quantity already set up in the computing system. Ordering in this context can refer to local replenishment of this surgical suite from a local storeroom, e.g., in a hospital, to hospital-wide replenishment of the local storeroom, or both. This process is repeated for each type of disposable item used in the surgical process until the operation is complete.

Figure 4:
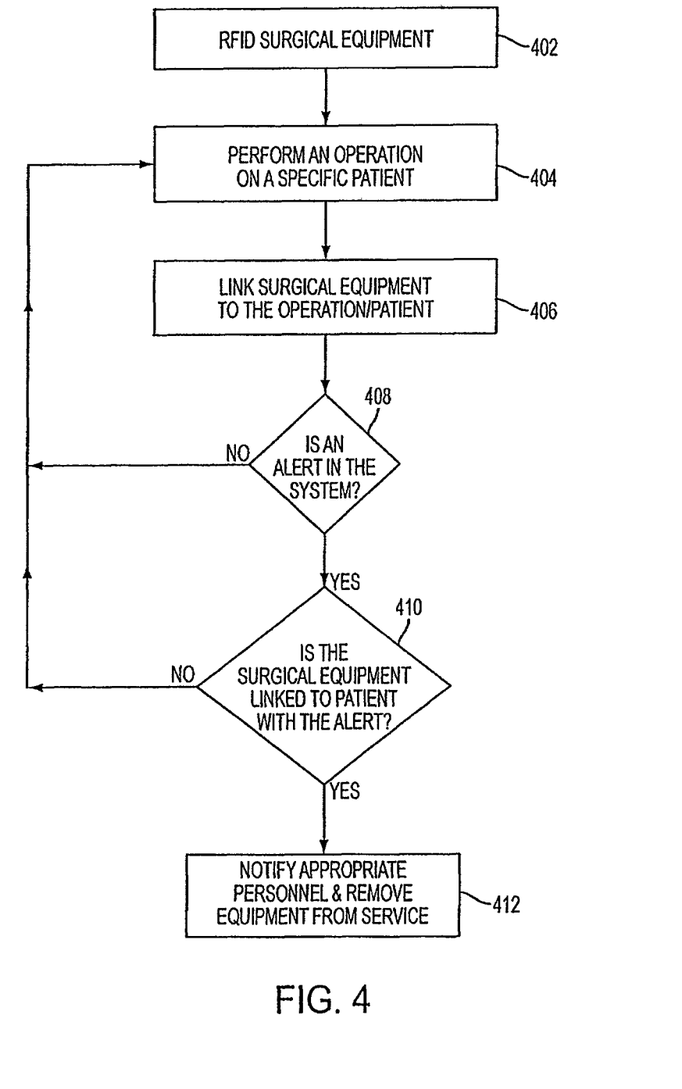
FIG. 4 is a flow chart illustrating an alert system according to exemplary embodiments.

According to another exemplary embodiment of the present invention, the specific surgical tools used on a patient during an operation are linked together and stored in a database. Tracking this information can be useful because when a patient is determined to have a certain type of condition, such as a prion disease (Bovine Spongiform Encephalopathy), any surgical equipment that comes into contact with the patient during a procedure is required to be taken out of service (destroyed). As previously described a computing system is in communication with a surgical table and the surgical table is capable of reading the RFID tag of equipment used in the area. An exemplary method will be described with respect to the flowchart of FIG. 4. Initially all surgical equipment has a RFID tag (step 402). An operation is performed upon a patient at step 404. A computing system receives the information regarding the surgical equipment that was used during the operation from the surgical table. Pertinent information, such as information regarding patient, operation, surgical equipment used and date, is linked together and saved in a database at step 406. Periodically, and prior to using surgical equipment in a new surgery, the system checks to determine if an alert has been entered into the system at step 408. The alert can be manually entered by a physician or nurse via a computing device or can be automatically generated by the system based upon a surgical procedure being pre-categorized as requiring device, equipment or material destruction. An alert relates to the need to find and remove a set of surgical equipment from use for any reason, such as surgical equipment used upon a patient with a prion disease. If no alert is found, the new operation can begin. If an alert is found, the system determines if the surgical equipment about to be used is linked to the patient associated with the alert at step 410. If there is no link between the surgical equipment and the patient with the associated alert, the new operation can begin. If there is a link between the surgical equipment and the patient associated with the alert, appropriate personnel are notified and the surgical equipment is removed from service at step 412. Alternatively, anytime an alert is entered into the system, the system can immediately notify the appropriate personnel to go and remove the identified surgical equipment from service.

Figure 5:
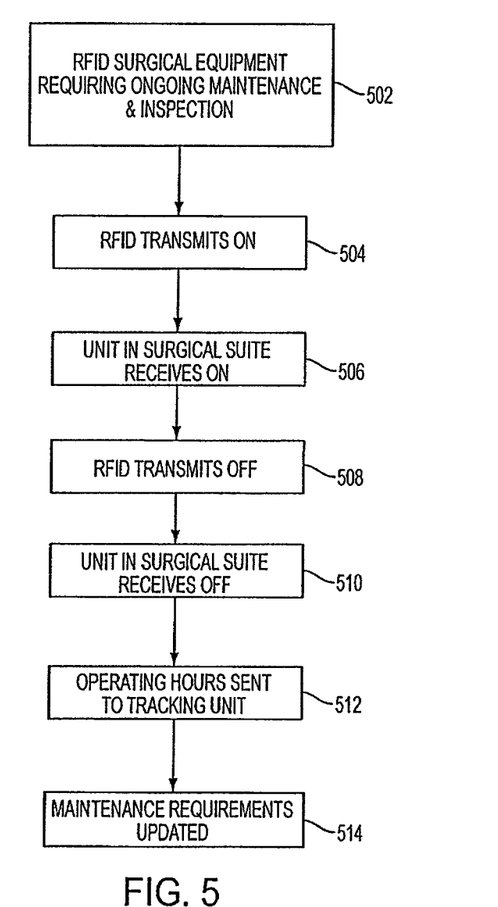
FIG. 5 is a flow chart describing a method for tracking equipment usage according to exemplary embodiments.

According to another exemplary embodiment of the present invention operational usage of equipment in a surgical suite can be tracked using RFID tags. This accurate method of tracking equipment operational usage will allow for timely maintenance to be performed. A computing system can be provided in the surgical suite that is coupled to a sensor capable of receiving RFID tag information from equipment in the surgical suite. An exemplary method for tracking equipment usage is shown in FIG. 5 and described below. RFID tags are attached to all (or substantially all) surgical equipment, such as an electrocardiogram machine, in the surgical suite for which the tracking of operating hours is desired at step 502. Upon powering up a device for use, the device RFID transmits a signal at step 504. At step 506, this signal is received by the computing system and a start time is associated with the equipment that generated the RF signal. At step 508, the device is powered of and another RFID device transmits a signal. This signal is received by the computing system and an end time for the device is generated at step 510. The computing system then sends the operational time to a database which tracks usage hours by equipment at step 512. Finally, maintenance requirements are updated as necessary in step 514. This exemplary method allows equipment usage to be accurately tracked, which in turn allows preventative maintenance to be performed at the times recommended by the equipment manufacturer or others. Additionally, it allows people to not use equipment that has been operating for too long between maintenance periods. According to an alternative embodiment, instead of using RFID tags to transmit separate signals when a device is turned on and when a device is turned off, one RFID tag can be used to transmit continuously while the device is powered up. Upon powering the device down, the RF signal ceases, which is recognized by the computing system allowing the computing system to accurately log how many hours a device has been in an on condition.

Figure 6:
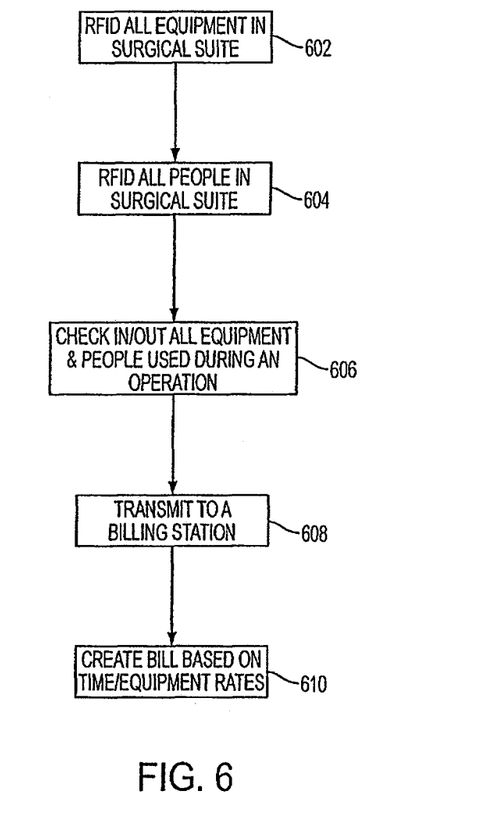
FIG. 6 is a flow chart describing a billing system according to exemplary embodiments.

According to another exemplary embodiment of the present invention, all equipment and personnel in a surgical suite during an operation can have a unique RFID tag associated with them. Combining this RFID tagging system with a method of checking items being used in and out of the zone of usage provides the ability to count the hours of specific equipment usage for billing purposes. This system is similar to the system described above for tracking equipment operational time for maintenance purposes. An exemplary method for this billing tracking feature is described below with respect to the flowchart in FIG. 6. Initially, at step 602 all equipment (including disposable equipment) is equipped with an RFID tag. At step 604, all people entering the surgical suite have an RFID tag attached to them. These RFID tags are unique and can contain pertinent information for billing, such as, a job function, piece of equipment or a personnel identification/billing rate. Upon the start of the procedure, all people are checked in to the system. Additionally, equipment is checked in to the system when it is used or turned on for use at step 606. Upon completion of the procedure, at step 608, the hours for each billable item is sent to a billing station. At step 610, an accurate bill for the procedure is created based upon the collected hours and the rate for each person, piece of equipment and any other desired billing inputs.

According to another exemplary embodiment a surgeon's preferred tool set can be tracked and readied for an upcoming operation. A surgeon's preferred tool set can have an RFID tag attached to the container of the preferred tools. Upon entering the surgical suite, both the tool set and the surgeon can check into the system with their respective RFID tags. If the tool set matches the surgeon, the operation can proceed. If the tool set does not match the surgeon, a computing system can query a database to find the location of the tool set. The outcome of the query can be displayed on an output device which then allows for someone to either go and get the desired tool set or have another method of delivery occur.

In many of the exemplary embodiments described above, the surgical suite has a computing system and/or a sensor for receiving RFID information. This method of communicating the RFID is only one of many methods possible for capturing the desired information using RFID. Other variations could be used by a person skilled in the art. For example, the use of computing systems, databases, and coupling methods for communicating between devices are well known in the art, as well as many variations of the same, such as, for example wireline or wireless transmission. Additionally, RFID tags can be either passive or active and either method or both can be used in the exemplary embodiments described above with minor manipulation for a person skilled in the art. Moreover, the items which can be tagged with RFD tags according to these exemplary embodiments can include any and all items which may be used in a surgical (or other medical) procedure, e.g., including drugs and medications. Further, systems in accordance with these exemplary embodiments, can be combined with other monitored items or information (such as vital signs), to create a virtual reproduction of a given surgery or other medical procedure, to track all of the items used and their location throughout the surgery event.

Figure 7:
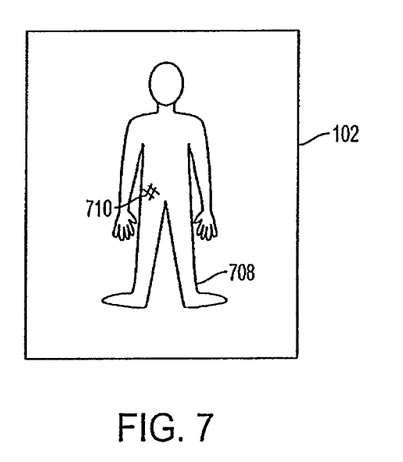
FIG. 7 depicts a projected visual indicator which shows the location of a tagged surgical item according to an exemplary embodiment.

According to yet another exemplary embodiment of the present invention, the object location information obtained by the computing device 108 from interrogating the RFID tags in a particular surgical suite can be used to provide feedback to the medical personnel performing a medical procedure therein. For example, a projector (not shown) can be connected to the computing device 108 and attached, e.g., to a ceiling of the surgical suite. The projector can be used to provide a visual indication of the location of a requested object within the surgical suite. For example, if a doctor or nurse wants to know the location of a particular sponge (or all sponges) that are in the surgical suite, an appropriate input can be made to the computing device 108 requesting that the location of that surgical sponge be pinpointed by the projector. The projector can then provide a visual indication of the precise location of that surgical sponge. For example, as shown in FIG. 7, the projector (not shown) can project an icon 710 which shows the precise location of a surgical sponge within patient 708 on surgical table 102. This facilitates the subsequent procedure to remove the sponge. Alternatively, if the requested item or object is not located within the surgical suite, the processor can emit an audible or visual alarm to alert the personnel that a requested object is not found. Inputs and outputs to the computing device 108, e.g., to request the projector to provide a visual indicator as described above, can be made using, e.g., keyboard data entry or voice inputs.

Those skilled in the art will appreciate that the techniques described above in the foregoing exemplary embodiments can be applied in other ways to generate other exemplary embodiments. For example, from a structural point of view, the RFID sensors described above may alternatively (or additionally) be provided within objects other than a surgical table, including (but not limited to) a portable handheld unit (e.g., wand), a container (e.g., trash can), other types of furniture (e.g., desk, chair), other apparatus (e.g., PDA, cellphone, etc.). Additionally, the various functions described above can be implemented separately in both a physical and logical sense. For example, the billing function described above can stand alone with respect to the scanning function, and vice versa.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims. No element, act, or instruction used in the description of the present application should be construed as critical or essential to the invention unless explicitly described as such. Also, as used herein, the article "a" is intended to include one or more items.

What is claimed is:

1. A method comprising:
    identifying, via a computing device, an allowable zone in a patient's body based on a type of surgical procedure in which a surgical item is to be used;
    determining, via the computing device, a location of the surgical item;
    determining, via the computing device, when the location of the surgical item is outside the allowable zone; and
    triggering, via the computing device, an alarm to indicate that the surgical item is outside the allowable zone, when the location of the surgical item is outside the allowable zone.

2. The method of claim 1, further comprising:
    associating the type of surgical procedure to a patient.

3. The method of claim 1, wherein the determining the location of the surgical item comprises interrogating a tag to determine the location of the surgical item.

4. The method of claim 1, further comprising:
    identifying a zone in which the surgical item is not to be used.

5. The method of claim 1, further comprising:
    matching the surgical item to the type of surgical procedure.

6. The method of claim 5, further comprising:
    producing an alarm when the surgical item does not match the type of surgical procedure.

7. The method of claim 1, further comprising:
    billing for the surgical item used for the type of surgical procedure.

8. The method of claim 1, further comprising:
    determining an inventory of the surgical item.

9. The method of claim 1, further comprising:
    comparing a remaining inventory of the surgical item to a reorder point; and
    when the remaining inventory is below the reorder point, ordering a new inventory of the surgical item.

10. A system, comprising:
    a processor executing a program that causes the processor to perform operations, the operations comprising:
        identifying an allowable zone in a patient's body based on a type of surgical procedure in which a surgical item is to be used;
        determining a location of the surgical item;
        determining the location is outside the allowable zone; and triggering an alarm to indicate the surgical item is outside the allowable zone.

11. The system of claim 10, the operations further comprising:
associating the type of surgical procedure to a patient.

12. The system of claim 11, the operations further comprising:
producing an alarm when the type of surgical procedure does not match the patient.

13. The system of claim 10, wherein the determining the location of the surgical item comprises interrogating a tag to determine the location of the surgical item.

14. The system of claim 10, the operations further comprising:
identifying a zone in which the surgical item is not to be used.

15. The system of claim 10, the operations further comprising:
matching the surgical item to the type of surgical procedure.

16. The system of claim 15, the operations further comprising:
producing an alarm when the surgical item does not match the type of surgical procedure.

17. The system of claim 10, the operations further comprising:
billing for the surgical item used for the type of surgical procedure.

18. The system of claim 10, the operations further comprising:
determining an inventory of the surgical item.

19. The system of claim 10, the operations further comprising:
comparing a remaining inventory of the surgical item to a reorder point; and
when the remaining inventory is below the reorder point, ordering a new inventory of the surgical item.

20. The system of claim 10, the operations further comprising:
tracking a time the surgical item was used during a surgical procedure.

\* \* \* \* \*